(12) United States Patent
Chin et al.

(10) Patent No.: US 9,795,408 B2
(45) Date of Patent: Oct. 24, 2017

(54) CATHETER WITH VESSEL LINING AND METHODS FOR USING SAME

(71) Applicant: Cruzar Medsystems, Inc., Braintree, MA (US)

(72) Inventors: Albert K. Chin, Palo Alto, CA (US); Thomas Kramer, San Carlos, CA (US)

(73) Assignee: Cruzar Medsystems, Inc., Braintree, MA (US)

( * ) Notice: Subject to any disclaimer, the term of this patent is extended or adjusted under 35 U.S.C. 154(b) by 440 days.

(21) Appl. No.: 14/449,739

(22) Filed: Aug. 1, 2014

(65) Prior Publication Data

US 2014/0343593 A1     Nov. 20, 2014

Related U.S. Application Data

(63) Continuation-in-part of application No. 14/073,270, filed on Nov. 6, 2013, now Pat. No. 9,326,790, which
(Continued)

(51) Int. Cl.
*A61B 17/34*     (2006.01)
*A61M 25/01*    (2006.01)
(Continued)

(52) U.S. Cl.
CPC ...... *A61B 17/3403* (2013.01); *A61B 17/3439* (2013.01); *A61B 17/3468* (2013.01);
(Continued)

(58) Field of Classification Search
CPC ....... A61B 2017/3435; A61B 1/00151; A61M 2025/1065; A61M 25/0119;
(Continued)

(56) References Cited

U.S. PATENT DOCUMENTS 3,669,099 A    6/1972   Silverman
3,831,587 A *  8/1974   Boyd ................ A61B 1/00082
                                              600/184
(Continued)

FOREIGN PATENT DOCUMENTS

EP      0227583    7/1987
EP      0359489    3/1990
(Continued)

OTHER PUBLICATIONS

European Search Report issued in European Application No. 15178491.5 dated Mar. 18, 2016.
(Continued)

*Primary Examiner* — Nathan R Price
*Assistant Examiner* — Anh Bui
(74) *Attorney, Agent, or Firm* — Greenberg Traurig, LLP; Chinh H. Pham; Roman Fayerberg

(57) ABSTRACT

Systems for providing access across a site of obstruction and methods for manufacturing and using such systems. Such systems may include a sleeve having an inflation lumen; a bushing disposed in a distal section of the sleeve; and an everting member coupled to the sleeve with the bushing, the everting member being movable from an inverted position inside the sleeve to an everted position outside the sleeve in response to an increase in pressure in the inflation lumen.

4 Claims, 19 Drawing Sheets

Related U.S. Application Data is a continuation-in-part of application No. 13/267,657, filed on Oct. 6, 2011, now Pat. No. 8,926,559.

(60) Provisional application No. 61/390,301, filed on Oct. 6, 2010.

(51) Int. Cl.
*A61M 25/06* (2006.01)
*A61M 25/10* (2013.01)

(52) U.S. Cl.
CPC ..... *A61M 25/0119* (2013.01); *A61M 25/0662* (2013.01); *A61M 25/104* (2013.01); *A61M 25/1006* (2013.01); *A61M 2025/0681* (2013.01); *A61M 2025/1081* (2013.01)

(58) Field of Classification Search
CPC ...... A61M 25/1006; A61M 2025/0681; A61M 2025/1081
See application file for complete search history.

(56) References Cited

U.S. PATENT DOCUMENTS

| | | | |
|---|---|---|---|
| 3,911,927 | A | 10/1975 | Rich et al. |
| 4,109,659 | A | 8/1978 | Sheridan |
| 4,254,774 | A | 3/1981 | Boretos |
| 4,493,711 | A | 1/1985 | Chin et al. |
| 4,630,609 | A * | 12/1986 | Chin ............... A61M 25/104 604/101.01 |
| 4,863,440 | A * | 9/1989 | Chin ............... A61M 25/0119 604/271 |
| 4,871,358 | A | 10/1989 | Gold |
| 5,171,305 | A * | 12/1992 | Schickling ......... A61M 25/0119 604/271 |
| 5,295,960 | A | 3/1994 | Aliahmad et al. |
| 5,458,573 | A | 10/1995 | Summers |
| 6,979,290 | B2 | 12/2005 | Mourlas et al. |
| 8,491,519 | B2 | 7/2013 | Chin |
| 8,926,559 | B2 | 1/2015 | Chin |
| 2002/0120226 | A1 | 8/2002 | Beck |
| 2003/0144629 | A1 | 7/2003 | Hawk et al. |
| 2005/0049718 | A1 | 3/2005 | Dann et al. |
| 2011/0213469 | A1 | 9/2011 | Chin et al. |
| 2012/0302996 | A1 | 11/2012 | Barash |

FOREIGN PATENT DOCUMENTS

| | | |
|---|---|---|
| EP | 1494524 | 1/2005 |
| GB | 1482873 | 8/1977 |
| WO | 0183017 | 11/2001 |
| WO | 03/084584 A2 | 10/2003 |
| WO | 03/084584 A3 | 10/2003 |
| WO | 2011088381 | 7/2011 |

OTHER PUBLICATIONS

International Search Report and Written Opinion for International Application No. PCT/US11/55149 dated Jan. 23, 2012.
Office Action issued for U.S. Appl. No. 13/267,657 dated Oct. 9, 2012.
Extended European Search Report issued for European Application No. 11831624.5 dated Feb. 26, 2014.
Partial European Search Report issued in European Application No. 1517849.5 dated Dec. 21, 2015.

* cited by examiner

CATHETER WITH VESSEL LINING AND METHODS FOR USING SAME

RELATED APPLICATIONS

This application is a continuation in part of U.S. application Ser. No. 14/073,270, filed on Nov. 6, 2013, which is a continuation in part of U.S. application Ser. No. 13/267,657, filed on Oct. 6, 2011, which claims the benefit of and priority to U.S. Provisional Application No. 61/390,301, filed Oct. 6, 2010. All of these applications are incorporated herein by reference in their entireties.

BACKGROUND

Obstructions within body cavities and vessels can often inhibit access through the cavities and vessels. For example, atherosclerosis and other circulatory diseases occur when the arteries become narrowed or blocked. Plaque formation within the arteries can cause occlusive lesions or other obstructions on the artery wall. Similarly, clots, thrombus, stenosis, or tortuosity in a vessel can also act to inhibit access or movement through the vessel.

Such an obstruction can also cause health problems by impeding movement of fluid through the vessel. For example, if the vessel is a blood vessel, the obstruction may impede blood flow.

In addition, the ability of the obstruction to block the vessel can also create issues during surgery. For example, during a surgical procedure (e.g., angioplasty, stent placement, or other procedures within a cavity or vessel) a surgeon may require access, along the vessel, to a site distal to the obstruction. In other situations, a surgeon may wish to deliver a stent, catheter, or other device to the site of obstruction so that fluid, surgical devices, and/or other material can move across the obstruction. However, it can often be difficult to pass a catheter or other devices across the area of obstruction in the presence of an obstruction in the vessel. Repeated attempts and increased advancement force can be dangerous, as such acts may result in vessel perforation or laceration.

Accordingly, it would be desirable to have a system that can provide access across an obstruction in a vessel in order to provide easier passage through the vessel while minimizing potential damage to the vessel walls.

SUMMARY OF THE INVENTION

In some embodiments, a system for providing access across a site of obstruction, the system may include a sleeve having an inflation lumen; a bushing disposed in a distal section of the sleeve; and an everting member coupled to the sleeve with the bushing, the everting member being movable from an inverted position inside the sleeve to an everted position outside the sleeve in response to an increase in pressure in the inflation lumen.

In some embodiments, the everting member is partially inverted into the bushing. In some embodiments, the system further comprises an anchoring member coupled to the sleeve, the anchoring member being in fluid communication with the inflation lumen and being expandable from a deflated position to an inflated position to anchor the sleeve near a site of obstruction when the inflation lumen is pressurized to an anchoring pressure sufficient to anchor the sleeve in proximity to a site of obstruction. The sleeve may comprise a flared distal portion sized to accept the bushing.

In some embodiments, a system for providing access across a site of obstruction may include a sleeve having a lumen; an everting member coupled to the sleeve; and a push assembly slidably disposed within the lumen of the sleeve and connected to a proximal end of the everting member to move the everting member from an inverted position inside the sleeve to an everted position outside the sleeve.

The system may, in some embodiments, further comprise a bushing disposed in a distal section of the sleeve to couple the everting member to the sleeve. The system may further comprise an anchoring member coupled to the sleeve, the anchoring member being in fluid communication with the inflation lumen and being expandable from a deflated position to an inflated position to anchor the sleeve near a site of obstruction when the inflation lumen is pressurized to an anchoring pressure sufficient to anchor the sleeve in proximity to a site of obstruction. The push assembly may include an inner sleeve member connected to the proximal end of the everting member and a rigid push tube extending proximally from the inner sleeve member. The system may further comprise a sealing member disposed between walls of the lumen and the push assembly to seal the lumen. The push assembly, in some embodiments, comprises an inner lumen configured to receive a guidewire therethrough.

In some embodiments, a method of assembling a system for providing access across a site of obstruction is provided. Such method may include the steps of placing a bushing inside an open ended balloon material; inverting the balloon material through the bushing; and inserting the bushing and balloon material assembly into a sleeve. In some embodiments, such method may also include a step of sealing an inverted end of the balloon material to create a balloon.

In some embodiments, a method of opening an occlusion is provided. Such method may include the steps of advancing a guidewire through a sleeve and a balloon inverted into an inflation lumen of the sleeve; gripping the guidewire with the balloon; and everting the balloon from the sleeve to distally advance the guidewire gripped by the balloon. In some embodiments, in the advancing step, the sleeve further comprises an anchoring member coupled to the sleeve, the anchoring member being in fluid communication with the inflation lumen and being expandable from a deflated position to an inflated position to anchor the sleeve near a site of obstruction when the inflation lumen is pressurized. In some embodiments, the everting step may comprise the steps of everting and re-inverting balloon to cyclically advance and retract the guidewire.

DETAILED DESCRIPTION

In accordance with various embodiments of the present invention, systems and methods are provided for providing access across an obstruction, such as an obstruction observed in connection with a complete or partial blockage within a vessel caused by, for instance, a clot, stenosis, or tortuosity within a blood vessel. The systems and methods described below may also, in some instances, be used to navigate past difficult regions in vessels, including arteries, veins, ureters, urethra, Fallopian tubes, pancreatic ducts, nasal sinuses, or any luminal structures or cavities in the body.

Figure 1:
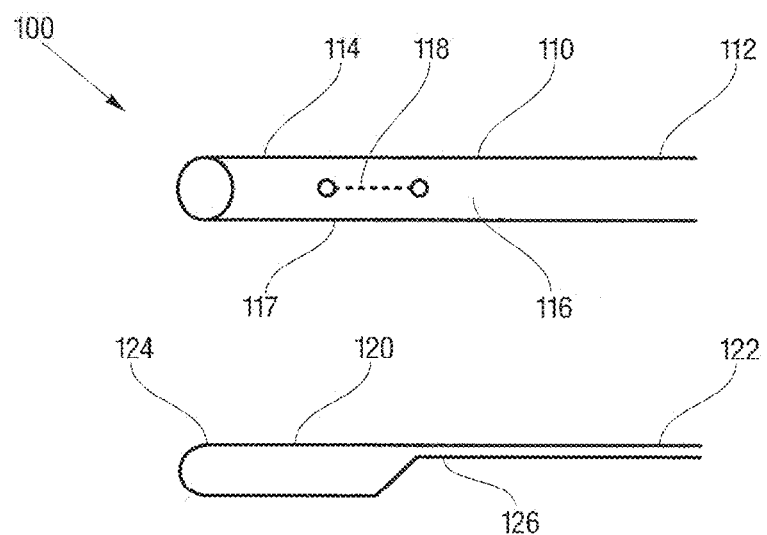
FIG. 1 illustrates various components of a system for providing access across an obstruction in accordance with an embodiment of the present invention.

FIG. 1 shows various components of a system 100 for providing access across an obstruction according to one embodiment of the present invention. System 100, in an embodiment, may include a sleeve 110 and a balloon 120.

The sleeve 110, in an embodiment, can include a proximal portion 112, an opposing distal portion 114, and a pathway 116 therebetween. The pathway 116, as illustrated, may extend across a juncture 117 between distal portion 114 and the remainder of sleeve 110. Also, as will be described, the distal portion 114 of the sleeve 110 may be designed to extend across a site of obstruction to provide access across the obstruction through pathway 116.

As illustrated in FIG. 1, sleeve 110 may be substantially tubular in shape. It should be noted, however, that while described as being tubular in shape, the sleeve 110 may have any other shape desired depending on the particular application, as the shape of the sleeve 110 may aid in the navigation of the sleeve 110 to provide access across a site of obstruction.

In some embodiments, sleeve 110 may be sufficiently flexible so that it can navigate through a tortuous path in a vessel. Additionally or alternatively, sleeve 110 may be sufficiently rigid so that it does not bend or fold in the presence of a proximal force being applied for advancing sleeve 110 through the vessel.

Sleeve 110 may also have any desired length, depending upon the application, so long as sleeve 110 can be advanced through a vessel to the site of obstruction. For example, in one embodiment, sleeve 110 may be relatively long, e.g. a long catheter, so that it can be advanced through a long or tortuous vessel to a site of obstruction. In another embodiment, sleeve 110 may be a relatively short sleeve that can be delivered across the obstruction. The sleeve 110 may also have any diameter sufficient to allow the sleeve 110 to fit within a vessel, depending upon the application and the size of the vessel. In an embodiment, the diameter of the sleeve 110 may remain substantially constant throughout. If desired, the diameter of the sleeve 110 may vary, as necessary, along the length of the sleeve 110.

In one embodiment, the sleeve 110 may further include a coating on an outer surface to reduce friction between the sleeve 110 and the vessel wall upon insertion into the vessel. In one embodiment, the coating may cover the entire outer surface of the sleeve 110. In an alternative embodiment, the coating may be locating only at the distal portion 114. Of course, the coating may be placed onto the outer surface in other manners as well. Likewise, the sleeve 110 may include a coating on an inner surface to reduce friction during eversion. In one embodiment, the inner coating may cover the entire inner surface of the sleeve 110. In an alternative embodiment, the coating may be locating only at the distal portion 114 of the sleeve 110. Of course, the coating may be placed onto the inner surface in other manners as well.

Figure 2A:
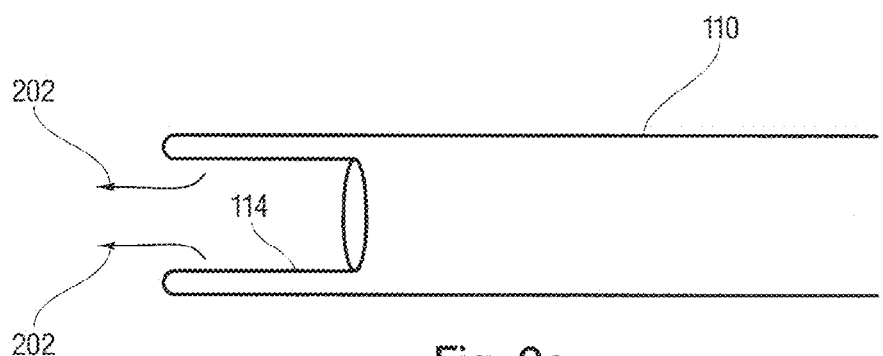
FIG. 2a-2b illustrate a sleeve, used in connection with the system of FIG. 1, for providing access across an obstruction in accordance with an embodiment of the present invention.
Figure 2B:
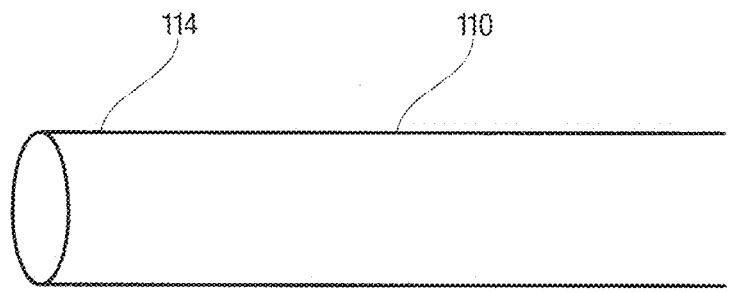

Distal portion 114 of sleeve 110, in an embodiment, may be designed to extend from sleeve 110 across a site of obstruction. In order to extend from sleeve 110, in some embodiments, distal portion 114 may be able to move from an inverted state to an everted state. Looking now at FIG. 2a, in an inverted state, distal portion 114 may be folded into sleeve 110. In this position, the length of sleeve 110 may be relatively shortened. However, during eversion, distal portion 114 may extend from the remainder of sleeve 110 by moving, as shown by arrows 202, from the inverted/folded in position of FIG. 2a, to an everted/extended position shown in FIG. 2b.

By providing a distal portion 114 that can evert in the manner described, distal portion 114 can extend across a site of obstruction to allow access to an area distal to the site. In particular, once distal portion 114 is extended across site, objects and devices, such as catheters, balloon catheters, plaque removal systems, etc., can be advanced through pathway 116 past the site of obstruction. Distal portion 114 of sleeve 110 may also provide protection to the vessel at the site of obstruction so that a device passing through sleeve 110 is less likely to damage the vessel in and around the site of the obstruction.

In order to extend across sites of obstruction that may have different sizes or lengths, distal portion 114 may, in one embodiment, have any desired length, depending upon the application. In one embodiment, distal portion 114 may be relatively long so that it can be everted to extend across a relatively long area of obstruction. In another embodiment, distal portion 114 may be relatively short, if a longer length is not required to provide access across the site of obstruction. Of course, providing a relatively long distal portion 114 within sleeve 110 and subsequently controlling the length or amount of eversion from sleeve 110, across the site of eversion, in order to accommodate the length of the obstruction, is also within the scope of the present invention.

As the distal portion 114 may need to fold, bend, or extend from an inverted state to an everted state, distal portion 114 may, in an embodiment, be made from a material that is sufficiently flexible and pliable to allow such folding, bending, and extending.

In some embodiments, distal portion 114 may be integral with the remainder of sleeve 110. As such, distal portion 114 may be molded or constructed as a single piece along with the remainder of sleeve 110. In other embodiments, distal portion 114 may be a separate piece that can be attached to the remainder of sleeve 110. In such embodiments, distal portion 114 may be attached to the remainder of sleeve 110 in any appropriate fashion, so long as distal portion 114 can be everted from within the remainder of sleeve 110.

In some embodiments, distal portion 114 and the remainder of sleeve 110 may be made from the same material. In other embodiments, distal portion 114 and the remainder of sleeve 110 may be made from different materials. For instance, in one embodiment, if desired, only the distal portion 114 of sleeve 110 may be made from a substantially flexible material that allows eversion, while the remainder of the sleeve 110 may be made from a less flexible material to minimize deformation of the sleeve 110 during delivery through the vessel.

Since the sleeve 110 and distal portion 114 are designed to be inserted into vessels of a human or animal body, the sleeve 110 and/or the distal portion 114, in an embodiment, can be made from a material that is biocompatible. The biocompatibility of the material may help minimize occurrence of adverse reactions due to use of the sleeve 110 within a vessel. Examples of suitable materials include various types of metals, plastics, or any other materials. In some instances, sleeve 110 may also be made from a bioadsorbable material so that sleeve 110 may remain in the body to be absorbed by the body over time.

Referring back to FIG. 1, to deliver the distal portion 114 of sleeve 110 and provide a pathway 116 across an site of obstruction, the system 100 of the present invention may also include a balloon 120 capable of exerting a force on distal portion 114 so as to move the distal portion 114 of sleeve 110 from an inverted position to an everted position. In some embodiments, balloon 120 may be positioned within sleeve 110, as discussed below, so that, as the balloon 120 is inflated, it can push against and evert distal portion 114 from within sleeve 110.

As shown in FIG. 1, the balloon 120, in an embodiment, may include a lumen 126 for inflating and deflating balloon 120. Lumen 126, as can be appreciated, may be a tube, for example, through which fluid can flow for inflating and deflating balloon 120. In some embodiments, lumen 126 may be permanently or detachably coupled to balloon 120. In some embodiments, lumen 126 may be integral with the balloon 120. To that end, balloon 120 and lumen 126 may be manufactured as a single unit. In some embodiments, as illustrated in FIG. 1, the single unit of, balloon 120 and lumen 126 may have a distal portion, i.e., the balloon 120, wider than the proximal portion, i.e. lumen 126. Alternatively, the single unit may be substantially uniform in diameter with balloon 120 and lumen 126 having similar diameters. It should also be noted that, in some embodiments, balloon 120 itself may have a variable diameter, as is described in more detail below. In some embodiments, the inflation tube may be made of a thin-walled material that allows the inflation tube to collapse into the smallest space within the sleeve 110 while deflated. One such material is PET; although any thin-walled material is acceptable.

Figure 3A:
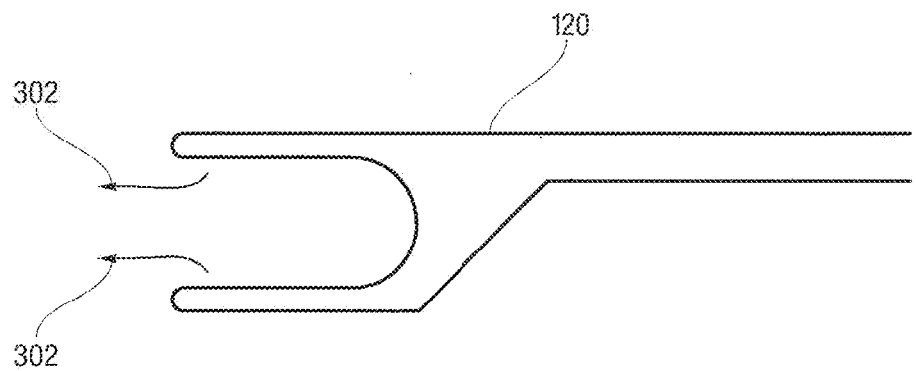
FIGS. 3a-3b illustrate a balloon, used in connection with the system of FIG. 1, for everting the sleeve in FIGS. 2a-2b across an obstruction in accordance with an embodiment of the present invention.
Figure 3B:
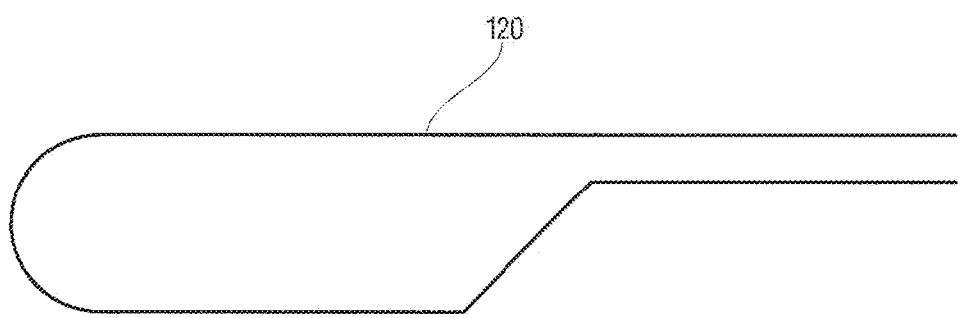

Now looking at FIGS. 3a-3, in order to evert distal portion 114 of sleeve 110, in an embodiment, balloon 120 may be designed to move from a inverted position to an everted position as it is inflated. As shown in FIG. 3a, in the inverted position, the balloon 120 may be inverted and folded into itself. As balloon 120 is inflated, balloon 120 may fill with a fluid (e.g. a liquid or gas) that can evert the distal end of balloon 120 so that balloon 120 extends, as shown by arrows 302, until it reaches a fully extended position, as shown in FIG. 3b. As balloon 120 extends, it may engage the inverted, distal portion 114 of sleeve 110, and act to push the distal portion 114 of sleeve 110 from an inverted position to an everted position. One skilled in the art will recognize that, rather than an inverted position, balloon 120 may also be folded, deflated, or otherwise compressed in other manners so that, once inflated, balloon 120 can push distal portion 114 of sleeve 110 from an inverted state to an everted state.

Figure 3C:
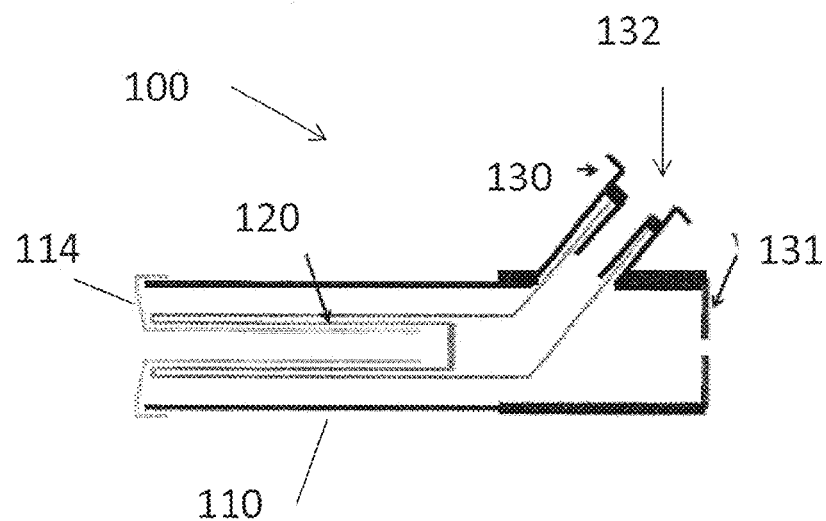
FIGS. 3c-3e illustrate a system for providing access across an obstruction in accordance with an embodiment of the present invention.
Figure 3D:
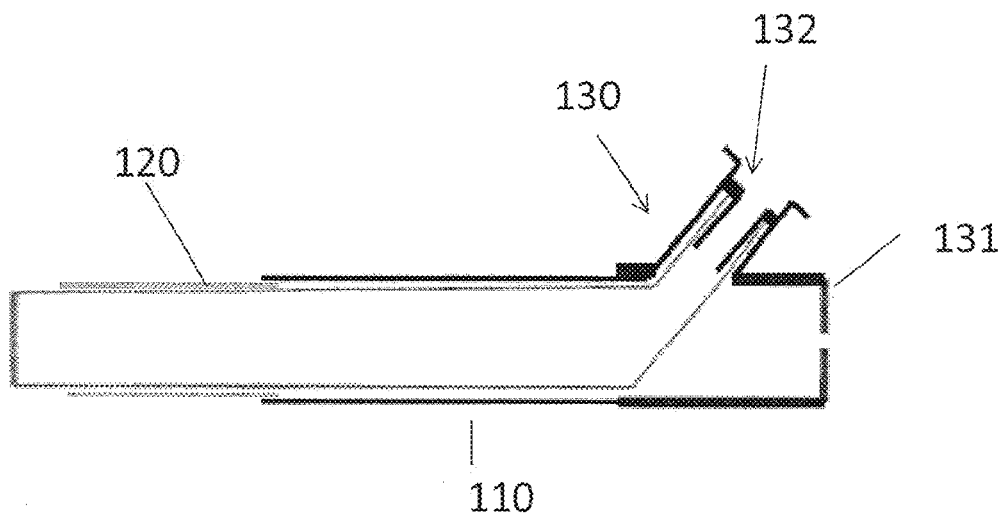

In reference to FIG. 3c, in some embodiments, the system 100 may include a connector 130 at the proximal end of sleeve 110 to facilitate coupling of lumen 126 to an inflation mechanism (not shown), that can direct fluid into and out of balloon 120 through lumen 126. The inflation mechanism may be a pump (e.g. a manual or automatic pump), syringe, or other device that can inflate and/or deflate balloon 120 during use. In some embodiments, connector 130 may have one more ports 131, 132. In some embodiments, port 132 may be utilized as an inflation port to inflate balloon 120. Lumen 126 may be connected to port 132 on the inside of sleeve 110 and an inflation mechanism may be connected to port 132 on the outside to fluidly connect balloon 120 to the inflation mechanism. Balloon 130 may be everted by pressurizing balloon 120 through inflation port 132, as shown in FIG. 3d. Of course, other locations for the inflation port are possible as long as fluids can enter with a sufficient force to deploy the balloon.

Figure 3E:
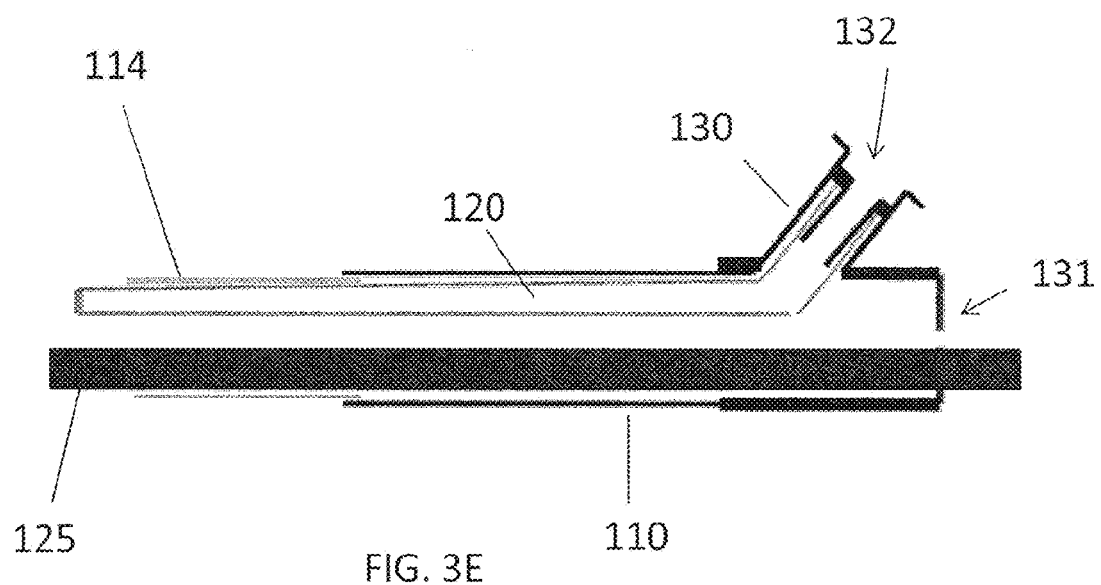

Connector 130 also enables introduction of surgical instruments or materials into sleeve 110 though port 133, as shown in FIG. 3e. In some embodiments, deflation of balloon 120 following eversion may collapse balloon 120 to enable a surgical instrument 125 to be advanced through sleeve 110. In some embodiments, ports 131, 132 may be sealable to provide a fluid seal between internal lumen of sleeve 110 and the ambient space.

Figure 4A:
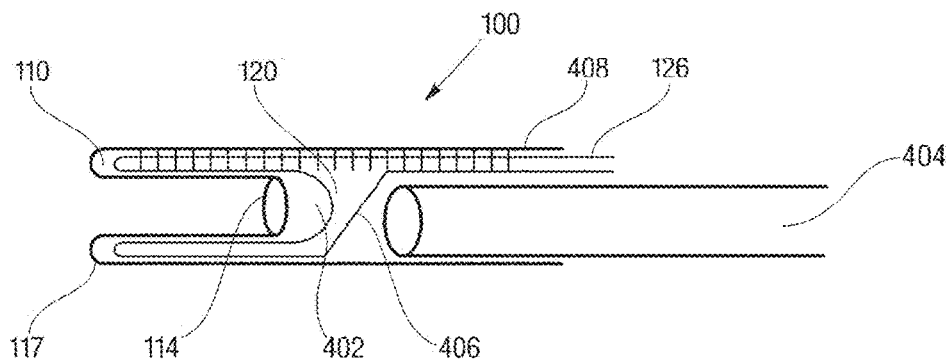
FIGS. 4a-4c illustrate a system for providing access across an area of obstruction in accordance with an embodiment of the present invention.

Referring to FIG. 4a, balloon 120 may be positioned in an inverted state within sleeve 110. In an embodiment, with the balloon 120 in an inverted state, the distal portion 114 of sleeve 110 may be folded into a pocket 402 formed by balloon 120. Folding distal portion 114 into pocket 402 may help to insure that distal portion 114 is properly secured therein for delivery.

It should also be noted that balloon 120, when inflated, may also minimize unwanted movement of sleeve 110 during eversion. For example, as distal portion 114 is everted, it may push against the obstruction and create a backward force, which may tend to push sleeve 110 (and/or balloon 120) backward through the vessel. However, as balloon 120 is inflated, it may press against the inner walls of sleeve 110 and hold the sleeve against the inner walls of the vessel, thus creating static friction between the sleeve and the vessel. The friction can act to anchor sleeve 110 in place so that sleeve 110 can withstand any backpressure without moving.

Figure 4B:
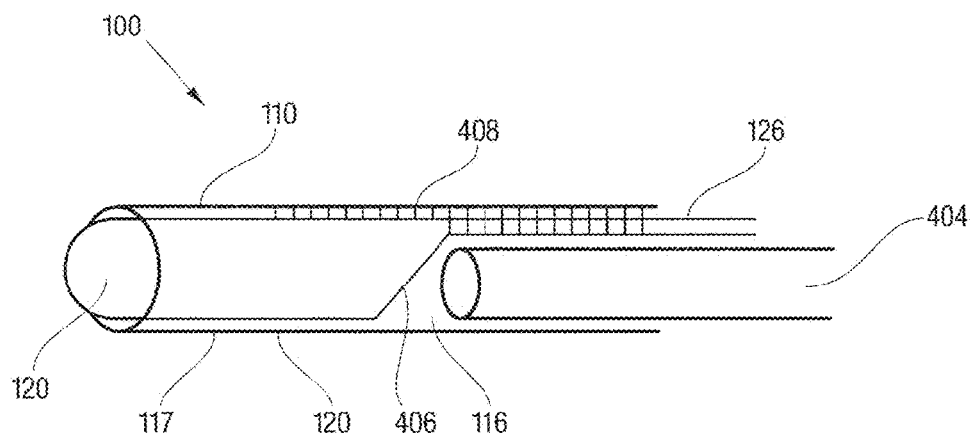

When inflated, the balloon 120 may extend in a substantially straight manner, as shown in FIG. 4B, to aid in extending the sleeve 110 past a site of obstruction. In other words, balloon 120 may have a substantially elongated shape so that, when inflated, balloon 120 expends in a substantially distal direction to aid in extending the distal portion 114 of the sleeve 110 past the site of obstruction.

Figure 5A:
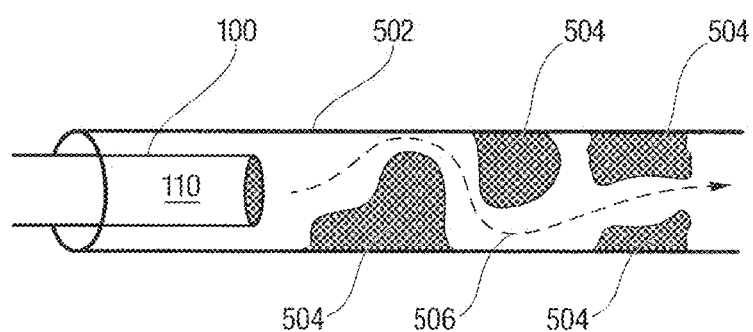
FIGS. 5a-5b illustrate a process for providing access across an area of obstruction in accordance with an embodiment of the present invention.

In one embodiment, as balloon 120 and distal portion 114 of sleeve 110 are designed to be flexible and pliable, balloon 120 and distal portion 114 may act to seek the path of least resistance through a site of obstruction. For example, turning to FIG. 5a, if a vessel 502 is blocked by a site of obstruction 504 (or series of obstructions 504), balloon 120, as it is everting, may seek the easiest path through the site of obstructions 504, as shown by arrow 506, since the fluid introduced into balloon 120 during inflation will tend to push balloon 120 and distal portion 114 of sleeve 110 through the site of obstruction following the path of least resistance. This may allow a user of system 100 to easily, blindly, or automatically find a path or opening through the site of obstruction 504 that would otherwise be difficult or impossible to find by probing the site with a guidewire or other device.

Figure 5B:
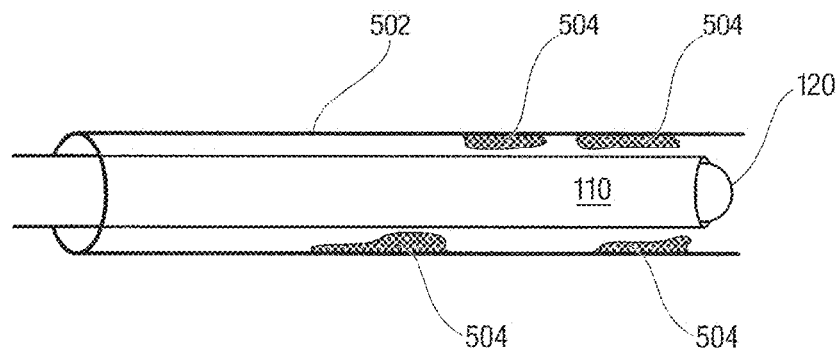

In one embodiment, as balloon 120 is everted through the site of obstruction, the balloon 120 may be designed to dilate or expand any obstruction at the site. As shown in FIG. 5b, as balloon 120 continues to inflate and push through the site of obstruction 504, the balloon 120 may widen the path through the site of obstruction 504 so as to clear a pathway through vessel 502. Of course, as balloon 120 dilates the site of obstruction 504, it may also act to evert sleeve 110 so that sleeve 110 creates a pathway through the vessel and across the site of obstruction 504.

Figure 4C:
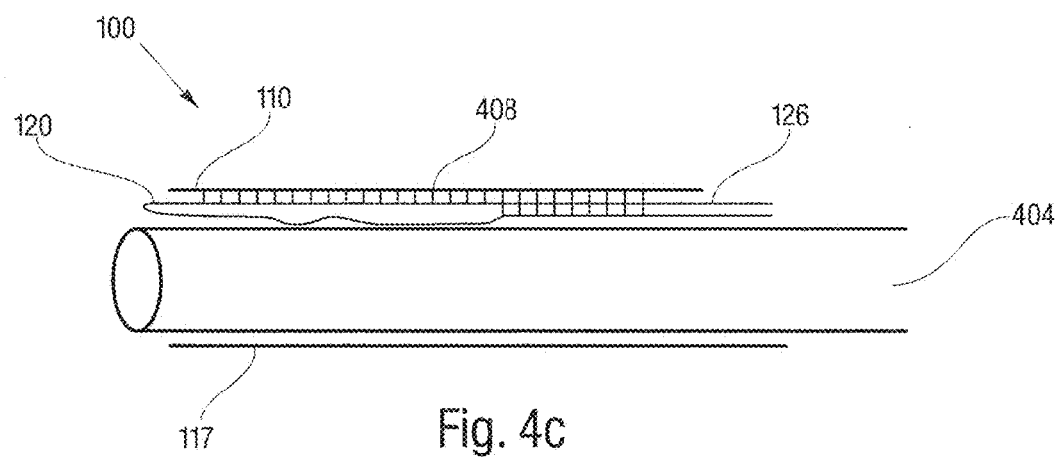

Now referring back to FIG. 4c, following eversion, the balloon 120 may be deflated to allow access along pathway 116 of sleeve 110 so that a device may be directed through sleeve 110. For example, as shown in FIG. 4c, balloon 120, when deflated, may have a smaller profile so that catheter 404 (or another device) may be advanced through sleeve and across the site of obstruction. In one embodiment, deflated balloon 120 may be situated adjacent to the inner wall of sleeve 110 to allow catheter 404 to pass. In other embodiments, balloon 120, when deflated, may be situated in other arrangements, or may be retracted and removed from sleeve 110 before catheter is advanced into or through sleeve 110, so long as catheter 404 can access the site of obstruction and/or a site distal to the obstruction.

In some embodiments, a deflation mechanism (not shown) may deflate balloon 120 by directing fluid out of balloon 120 through lumen 126. As discussed above, deflation mechanism may be a pump, syringe, or other device that can move fluid into and out of balloon 120. In other embodiments, balloon 120 may be designed so that catheter 404 (or another device) deflates balloon 120 by pushing balloon 120 aside as catheter 404 is advanced through sleeve 110. In such a design, balloon 120 may have a tapered wall (e.g. wall 406) so that, as catheter 404 pushes against wall 406, balloon 120 becomes squeezed or compressed between catheter 404 and the inner wall of sleeve 110. The squeezing action may deflate balloon 120 by pushing the fluid out of balloon 120 through lumen 126. Other methods of deflating balloon 120 may also be used. For example, if balloon 120 is no longer needed and/or disposable, a device may be advanced into sleeve to puncture balloon 120 so that it deflates.

To extend the sleeve 110 past an obstruction within a vessel, balloon 120 can be made from a flexible and sufficiently strong material capable of bypassing the obstruction. The balloon 120 should further be made from a sufficiently strong material capable of withstanding a sufficient force causing it to evert. The material of the balloon 120, in another embodiment, may be impermeable to fluids in order to allow the balloon 120 to withstand sufficient pressure. Since the balloon 120 is designed to be inserted within a vessel of a human or animal body, the balloon 120 should be made from a material that is biocompatible. The biocompatibility of the material may help minimize occurrence of adverse reactions due to use of the balloon 120 within a vessel.

The balloon 120 can further be made from any material that can aid in the eversion process. In one embodiment, the balloon 120 can be made from a material that minimizes resistance and friction so as to evert and bypass the obstruction with greater ease. For instance, the balloon 120 can be made from a material that is substantially smooth and/or has a relatively low coefficient of friction. Should it be desired, balloon 120 may further include a coating that can aid in eversion, inflation and deflation, or any other characteristic that may be desirable for the balloon 120. The coating may be applied to the balloon 120 on an inner surface, an outer surface, or a combination thereof.

The length of the balloon 120 may, in an embodiment, vary depending on a variety of characteristics. In certain instances, the length of the balloon 120 may be dependent on the length of the vessel. In other instances, the length of the balloon 120 may vary depending the length of distal portion 114. In yet other instances, the length of the balloon 120 may vary depending upon the length of the possible sites of obstruction. It should be noted that the length of the balloon 120 should permit the balloon 120 to fit within and/or evert the sleeve 110.

Similarly, the balloon 120 may also have any diameter desirable so long as the diameter allows the balloon 120 to fit within the sleeve 110 and the vessel. In some instances, balloon 120 may have a diameter sufficiently large so that, when inflated, it creates a fluid-tight seal against the inner wall of the sleeve. Balloon 120 may also have a diameter sufficiently large so that it can press sleeve 120 against the inner wall of a vessel. In one embodiment, the balloon 120 may have a diameter to allow the balloon 120 to substantially conform to the vessel walls when in an inflated state. However, in the inflated state, the diameter of the balloon 120 may also be smaller than the diameter of the sleeve 110, to minimize the likelihood of rupturing the sleeve 110. Of course, larger or smaller diameters may also be possible.

The balloon 120 may also have any shape desirable so long as the shape allows the balloon 120 to fit within the sleeve 110 and the vessel, and to evert distal end 114. In one embodiment, the balloon 120 may have a substantially tubular shape to allow the balloon 120 to substantially conform to the vessel. Of course, other geometric shapes are also within the scope of the present invention.

Referring again to FIGS. 4a-c, to minimize advancement or retreat of balloon 120 during eversion, the system 100, may include a coupling mechanism 408 that may act to couple a portion of the sleeve 110 to a portion of the balloon 120. The coupling mechanism may be designed to allow eversion of the balloon 120 while minimizing advancement or retreat of the balloon from within sleeve 110. Of course, in some embodiments, coupling mechanism may allow at least some axial movement of balloon 120 during eversion, if desired. The coupling mechanism may be any mechanism capable of securely coupling the balloon 120 and the sleeve 110. For instance, the coupling mechanism may be glue, tape, velco, clips, or any other commercially available mechanism. In other embodiments, coupling mechanism may be a mechanism that increases friction between balloon 120 and sleeve 110. For example, coupling mechanism may be a rough or perforated section of balloon 120 and/or sleeve 110 that creates friction when balloon 120 is inflated and pressed against sleeve 110.

Once sleeve 110 has been everted, sleeve 110 may provide a pathway 117 to permit an object, such as catheter 404, to be delivered across a site of obstruction. The pathway 116, in one embodiment, may extend across juncture 117 between distal end 114 and the remainder of sleeve 110 so that catheter 404 can access the site of obstruction, or access areas distal to the site of obstruction. To provide access across a site of obstruction, catheter 404, or another device, may be advanced along pathway 116 of the sleeve 110 toward the distal portion 114 of sleeve 110. In an embodiment, catheter 404 may be designed to provide sufficient structural integrity to sleeve 110 along its length, so as to minimize collapse, folding, or compaction of sleeve 110. In one embodiment, catheter 404 may be protected by the sleeve 110 as catheter 404 is advanced forward through the vessel, as shown in FIG. 4c. In an embodiment, catheter 404 may be any commercially available catheter, so long as it can be advanced along pathway 116 of sleeve 110. For instance, the catheter 404 may be a therapeutic catheter for delivering, for example, an intravascular stent, or a balloon catheter for angioplasty.

The present invention can be deployed, in accordance with one embodiment, using an endoscope (not shown). The endoscope may help guide the system 100 through the vessel to a site of interest. In an embodiment, the endoscope may be provided with a body positioning designed to be situated about the sleeve 110.

Figure 6A:
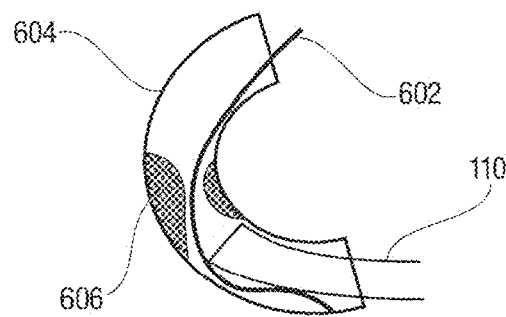
FIGS. 6a-6c illustrate a system for providing access across an area of obstruction in accordance with an embodiment of the present invention.
Figure 6B:
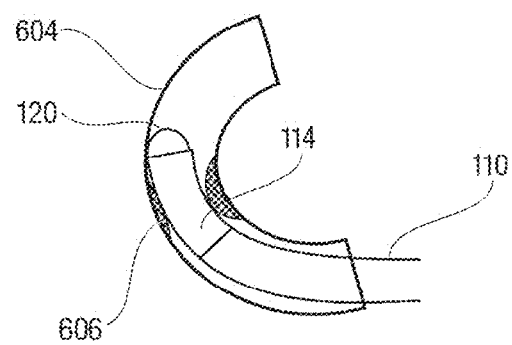
Figure 6C:
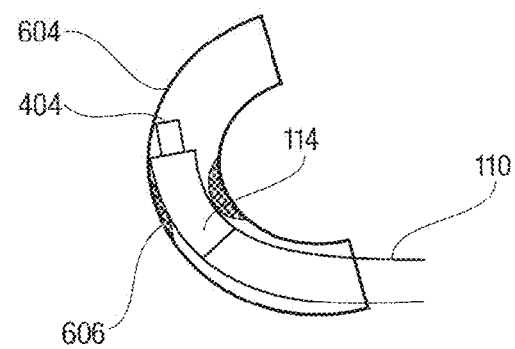

Looking now at FIGS. 6a-c, in other embodiments, the system 100 of the present invention may be designed to allow a guidewire (e.g. guidewire 602) to help guide and direct sleeve 110 through the vessel. In some embodiments, the guidewire may be designed to push the system 110 through a vessel to a site of interest. In such a design, system 100 may include a pocket or slot 118 (see FIG. 1) on its surface that can accommodate an end of guidewire 602. Guidewire 602 may be positioned within slot 118 so that, as guidewire 602 advances through vessel 604, guidewire 602 pushes sleeve 110 through vessel 604 to the site of obstruction 606. In another embodiment, slot 118 may allow sleeve 110 to slide along the length of guidewire 602. In such an embodiment, guidewire 602 may first be advanced into vessel 604 to the site of obstruction 606 (as in FIG. 6a), then sleeve 110 may be advanced along the length of guidewire 602 until sleeve 110 is positioned adjacent to the site of obstruction 606.

The guidewire 602, in an embodiment, may further be capable of positioning sleeve 110 adjacent to site of obstruction 606 so that the balloon 120 can evert sleeve 110 across the site of obstruction 606. It should be noted that while the guidewire 602 can be positioned in any manner to allow guidance of the sleeve 110, its design should minimize any obstructions of the balloon 120 and the sleeve 110 during eversion. In other words, guidewire 602 should be positioned so that it does not impede the eversion of distal end 114. In some embodiments, guidewires such as those described in U.S. Provisional Patent Application 61/435,517 (filed Jan. 24, 2011; incorporated herein by reference in its entirety), can be used to guide sleeve 110 to the site of obstruction 606. In another embodiment, the guidewire 602 may be any guidewire that is commercially available.

In another embodiment, the sleeve 110 may be used in conjunction with guidewire 602 so as to facilitate delivery of guidewire 602 across the site of obstruction 606. In such an embodiment, distal end 114 of sleeve 110 may be everted to provide a pathway 116 across the site of obstruction 606. Guidewire 602 may then be advanced through pathway 116 and across the site of obstruction 606. Subsequently, sleeve 110 may be removed, leaving guidewire 602 in place across the site of obstruction 606 so that guidewire 602 may be used as a track for advancement of other devices to or through the site.

In operation, to prepare the system 100 for insertion into the body, a balloon 120 may be positioned within a sleeve 110. Both the distal portion 114 of the sleeve 110 and a distal end of the balloon 120 can then be inverted so that the distal portion 114 of sleeve 110 is folded into the remainder of the sleeve. In some instances, balloon 120 may be inverted so as to create a pocket 402, within which distal portion 114 may sit. A catheter 404 may also be placed into the sleeve 110.

Once loaded, the system 100 may be inserted into a vessel in the body and advanced along the vessel 604 to a site of obstruction 606, as shown in FIG. 6a. Once at the site of obstruction 606, balloon 120 may be inflated so as to evert distal portion 114 and deliver it across the site of obstruction 606. Inflation of balloon 120 may require the direction of pressurized fluid into balloon 120 via a lumen 126 and/or an inflation port. As balloon 120 is inflated, it may push and evert the distal portion 114 of sleeve 110 from within sleeve 110 across the site of obstruction 606, as shown in FIG. 6b. In some instances, balloon 120 may also blindly or automatically seek a path through the site of obstruction 606 as it is inflated, as described above. Inflation can also open or widen a path through the site of obstruction 606 by causing balloon 120 to dilate the site. Following eversion, balloon 120 may be deflated and/or removed, and catheter 404 may be advanced through pathway 116 to access the site of obstruction, or an area distal to the site of obstruction, as shown in FIG. 6c.

Figure 7A:
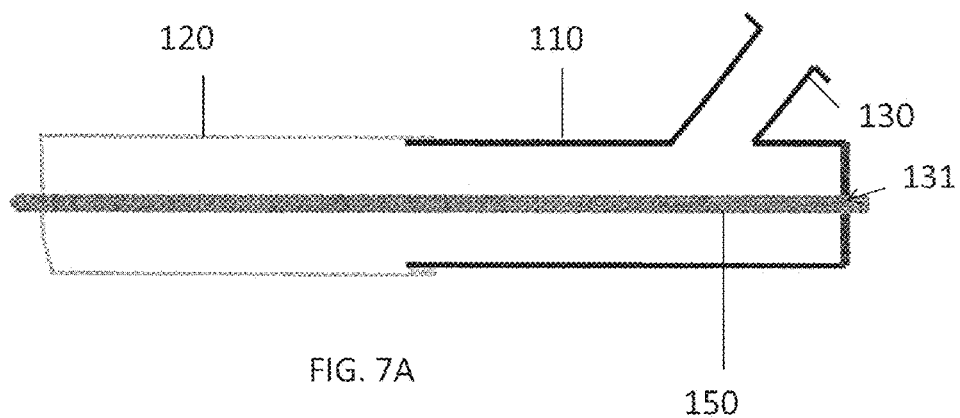
FIGS. 7a-7b illustrate a system for providing access across an area of obstruction in accordance with an embodiment of the present invention.
Figure 7B:
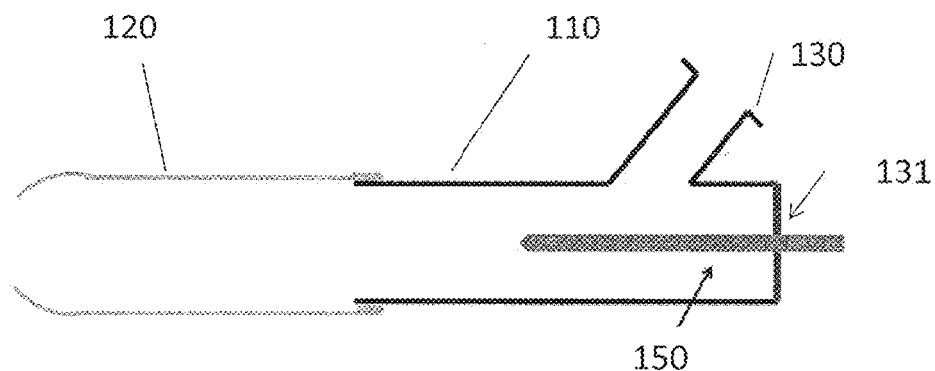

In reference to FIGS. 7a-7b, in some embodiments, balloon 120 may be used to form a pathway through the site of obstruction. To that end, once balloon 120 is everted from sleeve 110 and is positioned across a site of obstruction, balloon 120 may be punctured to open the distal end of balloon 120 to provide a lining across the site of obstruction thereafter. It should be noted that, when using this design, balloon 120 may be used instead of distal portion 114, as illustrated in FIGS. 7a-7b, to provide a pathway though the stenosis. Alternatively, in some embodiments, it may be useful to use balloon 120 as shown in FIGS. 7a-7b in addition to distal portion 114.

In some embodiment, a puncture wire 150 having sufficient length and strength may be provided to puncture the distal end of the inflated balloon 120. The wire may have a cross-sectional diameter that is less than the cross sectional diameter of sleeve 110. For example, puncture wire 150 may have a diameter between about 0.015 inches and about 0.025 inches. Puncture wire 150 may be made of a material having sufficient stiffness to allow the wire to puncture though distal end 124 of balloon 120. In some embodiments the wire may be made of stainless steel or a superelastic metal such as Nitinol; although, any material having the desired stiffness and flexibility is acceptable.

Puncture wire 150 may enter the system 100 through an opening of connector 130. In some embodiments, puncture wire 150 may have a length that is at least twice the length of the sleeve. This length can allow sleeve 110 to be removed from the vessel after puncture wire 150 has punctured balloon 120, and while the position of puncture wire 150 in the vessel is maintained. In this manner, puncture wire 150 may serve as a guide for a secondary device (not shown), such as a vascular stent placement catheter that can travel over puncture wire 150 through the vessel.

To secure the position of the system 100 at the site of interest, in some embodiments, the system 100 of the present disclosure may include an anchoring cuff to anchor the system in place during inflation and eversion of balloon 120 and distal portion 114.

Figure 8:
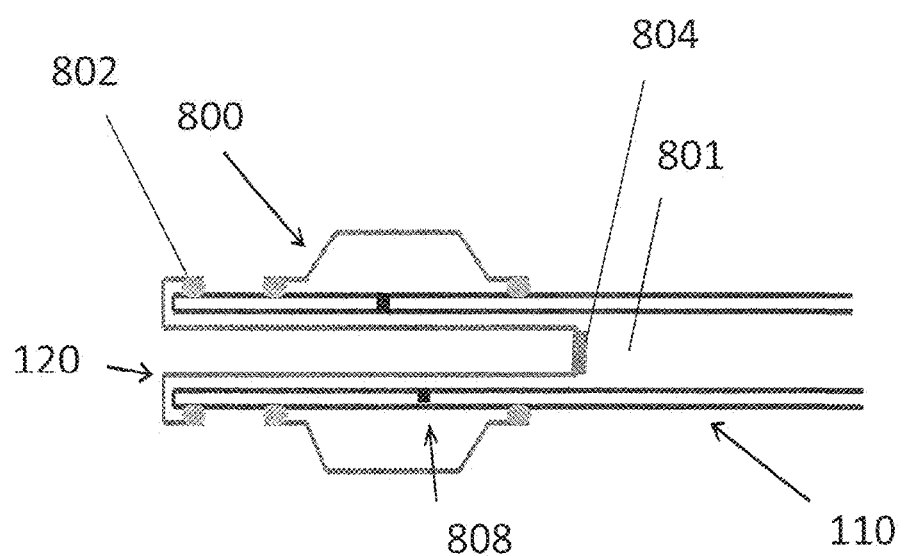
FIG. 8 illustrates a system for providing access across an area of obstruction in accordance with an embodiment of the present invention.

In reference to FIG. 8, in some embodiments, the systems 100 of the present disclosure may include an anchoring cuff 800 disposed on the outer surface of sleeve 110 to anchor system against surrounding vessel walls. Although shown with a single anchoring cuff 800, it should of course be understood that multiple anchoring cuffs 800 may be employed, as desired, for increased anchoring of system 100 inside the vessel. In some embodiments, anchoring cuff 800 may be positioned proximally to the distal tip of sleeve 110. As shown in FIG. 8, the anchoring cuff 800 may be independent from balloon 120. Anchoring cuff 800 may be in fluid communication with a lumen 801 of sleeve 110 to enable inflation or deflation of anchoring cuff 800 through sleeve 110. In some embodiments, a connector can be disposed at the proximal end of sleeve 100 to facilitate coupling of an inflation mechanism to lumen 801 for inflating or deflating anchoring cuff 800.

In some embodiments, balloon 120 may include an anchoring section 802 for coupling balloon 120 to sleeve 110. In some embodiments, the anchoring section 802 may be anchored to sleeve 110 on the outside of the sleeve 110. In some embodiments, the anchoring section 802 may be anchored to sleeve 110 on the inside of the sleeve 110. In some embodiments, anchoring section 802 may be coupled directly to sleeve 110, as shown in FIG. 8. In some embodiments, balloon 120 may be coupled to sleeve 110 using connector 130, as described above. Balloon 120 may also include an everting section 804 to be placed through a stenosis in the vessel.

In some embodiments, a single inflation lumen 801 may be used both for moving everting section 804 of balloon 120 from an inverted position to an everted position as well as for inflating anchoring cuff 800 to anchor sleeve 110 inside the vessel. In such an embodiment, anchoring cuff 800 may be in fluid communication with inflation lumen 801 through one or more holes 808 in the wall of sleeve 110. In this manner, anchoring cuff 800 may inflate first upon initial pressurization of sleeve 100 to anchor sleeve 110 against the vessel wall. In particular, the pressure introduced into anchoring cuff 800 may initially be equal to inflation pressure. The pressure in anchoring cuff 800 may then be allowed to increase until eversion pressure is reached, at which point everting section 804 of balloon 120 may evert from sleeve 110 into the everted position across stenosis in the vessel. The pressure in anchoring cuff 800 may be allowed to increase as is necessary to ensure that everting section is everted through the stenosis, while ensuring that system 100 does not recoil from the site of stenosis. It should be appreciated that eversion of everting section 804 may not necessarily occur until pressure within anchoring cuff 800 is at a level to provide sufficient anchoring of system 100, and additional pressure is directed to everting of everting section 804.

Such design may provide self-adjustment of pressure in anchoring cuff 800, which is equal to eversion pressure, upon pressurization with a single injection device. Injection of fluid into the catheter anchors the device prior to balloon eversion through the stenosis. If high pressure is required to evert balloon 120 and, if present, distal portion 114, through a tight stenosis, equivalent high pressure is maintained in anchoring cuff 800 to provide increased anchoring of sleeve 110 in position near the site of stenosis to prevent sleeve 110 from backing out during eversion of balloon 120 and distal portion 114 through the stenosis. Of course separate lumens may be provided for anchoring cuff 800 and balloon 120.

Figure 9A:
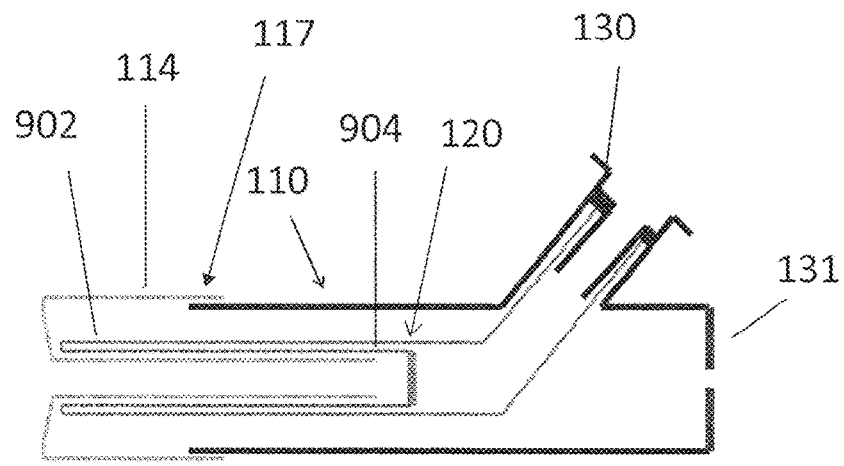
FIGS. 9a-9c illustrate a system for providing access across an area of obstruction in accordance with an embodiment of the present invention.
Figure 9B:
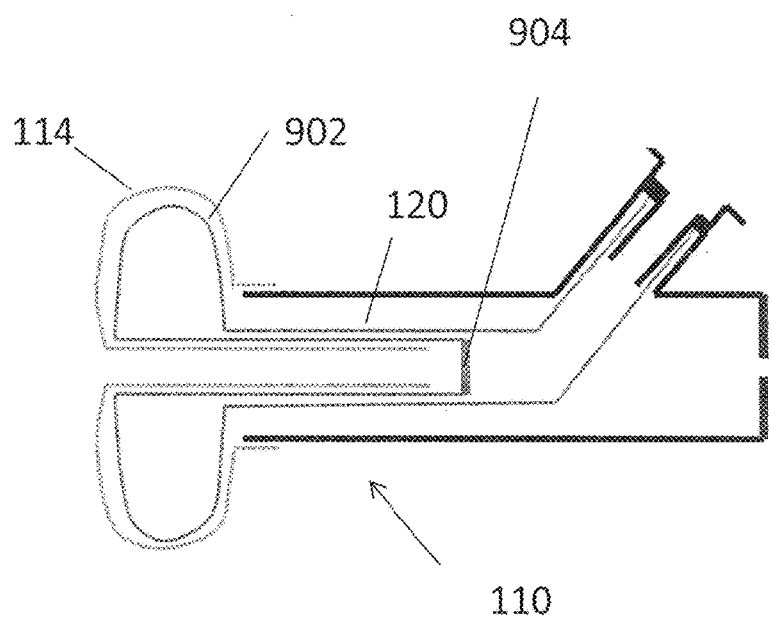
Figure 9C:
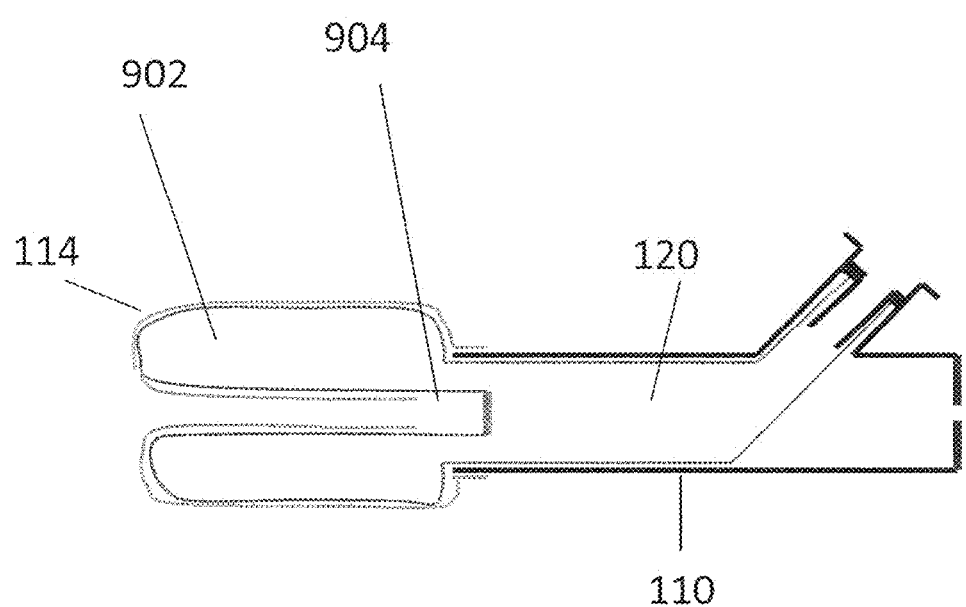

In some embodiments, as shown in FIG. 9a-9c, to anchor sleeve 110 inside the vessel, balloon 120 may include an anchoring section 902 for anchoring sleeve 110 inside the vessel and an everting section 904 to be placed through the stenosis in the vessel. In some embodiment, balloon 120 may have a variable diameter, with anchoring section 902 having a greater diameter than an everting section 904 of balloon 120.

In reference to FIGS. 9a-9c, in some embodiments, proximal end of balloon 120 may be connected to connector 130 at the proximal end of sleeve 110, as described above. Prior to inflation of balloon 120, as shown in FIG. 9a, anchoring section 902 of balloon 120 may extend distally beyond juncture 117 between distal portion 114 and the remainder of sleeve 110. When balloon 120 is initially inflated, anchoring section 902 may inflate first, as shown in FIG. 9b. The inflated diameter of anchoring section 902 may be equal to or slightly larger than the inner diameter of the vessel to allow anchoring section 902 to contact the wall of the vessel and hold sleeve 110 in position as everting section 904 everts through the stenosis or occlusion. Next, as shown in FIG. 9c, as the inflation of balloon 120 continues, everting section 904 of balloon 120 is everted from sleeve 110 to place distal portion 114 through the stenosis. In some embodiments, everting section 904 may have a smaller diameter than anchoring section 902 to enable everting portion 904 to fit through the narrowed section of the vessel. While not shown in FIGS. 9a-9c, in some embodiments, as described above, everting section 904 of balloon 120 may be punctured at the distal end to open everting section 904 to provide additional lining through the stenosis.

Figure 10A:
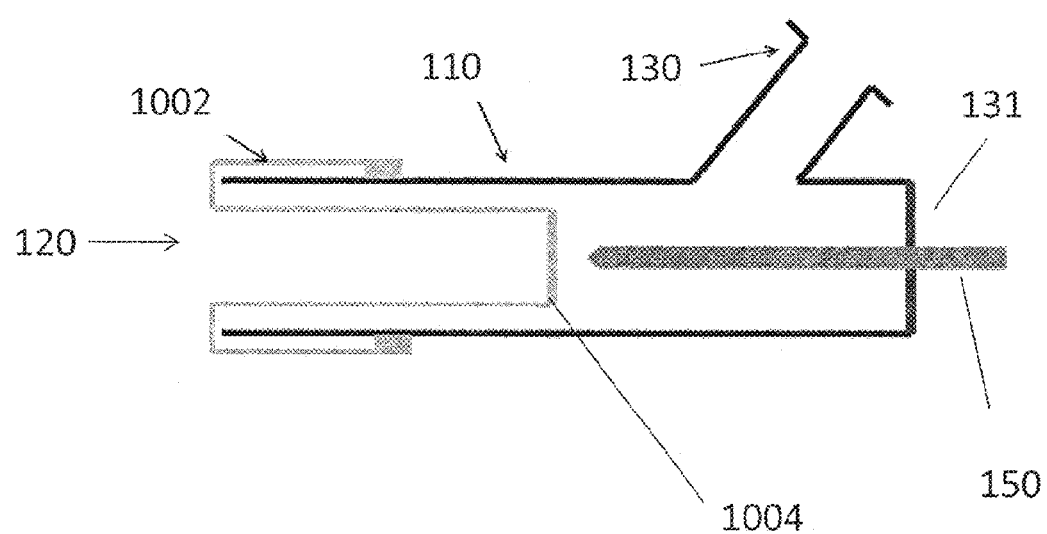
FIGS. 10a-10c illustrate a system for providing access across an area of obstruction in accordance with an embodiment of the present invention.
Figure 10B:
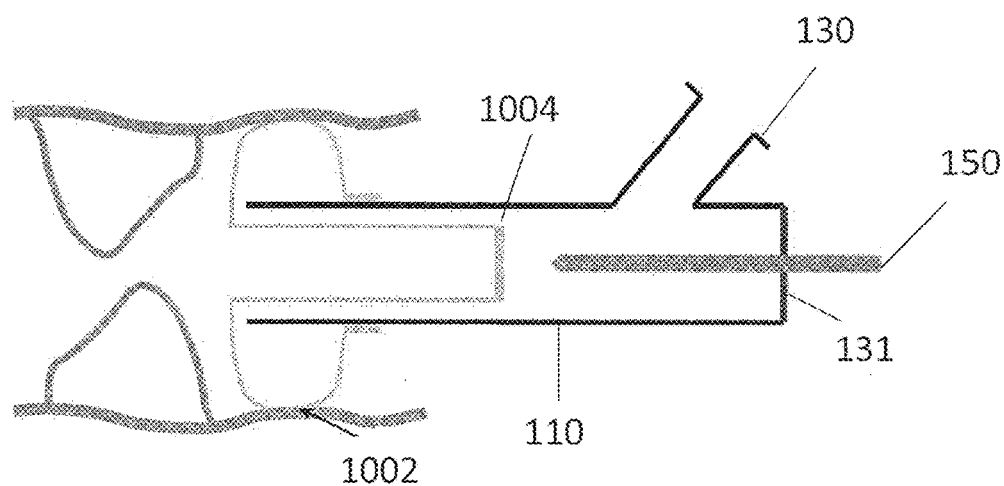
Figure 10C:
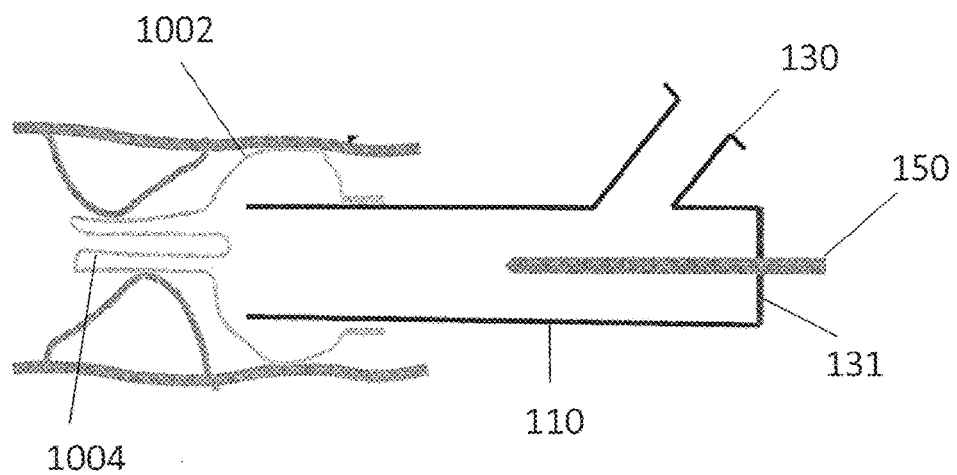

In reference to FIGS. 10a-10c, in some embodiments, proximal end of balloon 120 may be connected to distal end of sleeve 110, and used without distal portion 114 of sleeve 110. In such an embodiment, everting section 1004 of balloon 120 may be inverted into sleeve 110, as shown in FIG. 10a. When balloon 120 is initially inflated, an anchoring section 1002 may inflate first, as shown in FIG. 10b. The inflated diameter of anchoring section 1002 may be equal to or slightly larger than the inner diameter of the vessel to allow anchoring section 1002 to contact the wall of the vessel and hold sleeve 110 in position as everting section 1004 everts through the stenosis or occlusion. Next, as shown in FIG. 10c, as the inflation of balloon 120 continues, everting section 1004 of balloon 120 is everted from sleeve 110 and is, ultimately, positioned through the stenosis. In some embodiments, everting section 1004 may have a smaller diameter than anchoring section 1002 to enable everting portion 904 to fit through the narrowed section of the vessel. Finally, as described above, everting section 1004 of balloon 120 may be punctured at the distal end to open everting section 1004 to provide lining through the stenosis for passing surgical instruments through the stenosis.

Figure 11:
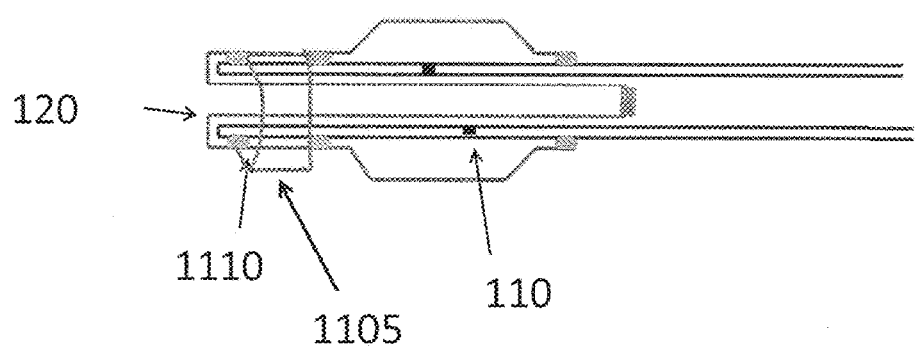
FIG. 11 illustrates a system for providing access across an area of obstruction in accordance with an embodiment of the present invention.

In reference to FIG. 11, in some embodiments, the instant system 100 may also include a guidewire sheath 1105. Guidewire sheath 1105 may be placed about sleeve 110. In some embodiments, guidewire sheath 1105 may be shaped and sized such that when guidewire sheath 1105 is positioned about sleeve 110, a lumen 1110 may be formed that may accommodate passage of a guidewire therethrough. Lumen 1110 may allow sleeve 110 to be advanced along a guidewire positioned in the vessel. In some embodiments, guidewire sheath 1105 may have multiple lumens, one lumen for inserting sleeve 110 into guidewire sheath 1105 to position guidewire sheath 1105 about sleeve 110 and one or more additional lumens for advancing a guidewire or other instruments through these additional lumens.

Figure 12A:
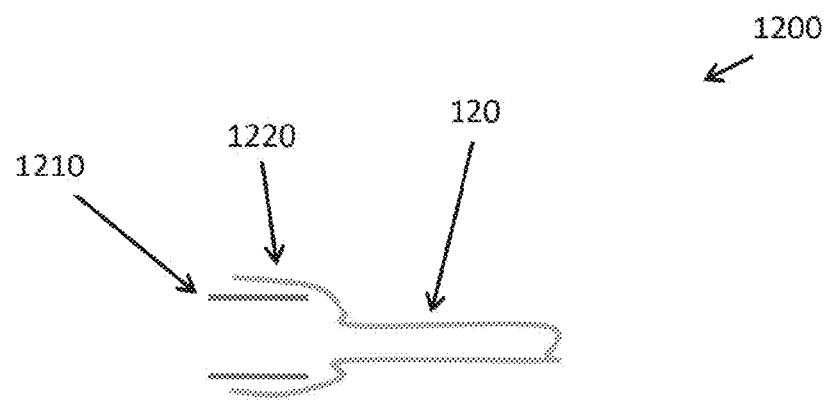
FIGS. 12a-12d illustrate a system for providing access across an area of obstruction in accordance with an embodiment of the present invention.
Figure 12B:
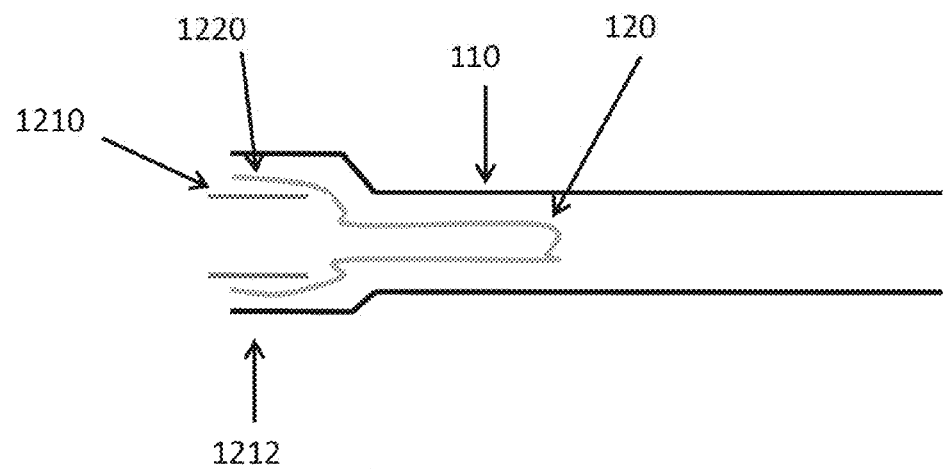

In reference to FIGS. 12a-12b, a balloon inversion subassembly 1200 may be provided for ease of inserting and coupling balloon 120 to sleeve 110. In some embodiments, the balloon inversion subassembly 1200 may include balloon 120 coupled to a bushing 1210. In some embodiments, balloon may be coupled to outside of bushing 1210 at anchoring sections 1220. The balloon inversion subassembly 1200 may be inserted into the distal end of sleeve 110 to couple balloon 120 to sleeve 110. In some embodiments, sleeve 110 may have a flared distal section 1212 to accept balloon inversion subassembly 1200. When balloon inversion subassembly 1200 is inserted into sleeve 110, bushing 1210 may press balloon material against the walls of sleeve 110 thereby coupling balloon 120 to sleeve 110.

Figure 12C:
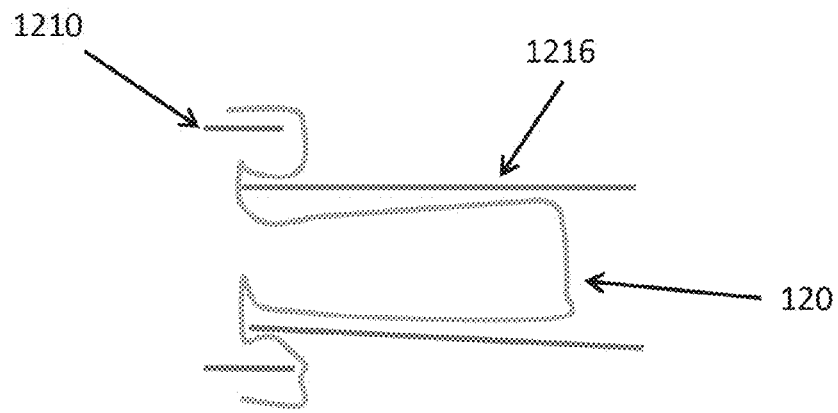
Figure 12D:
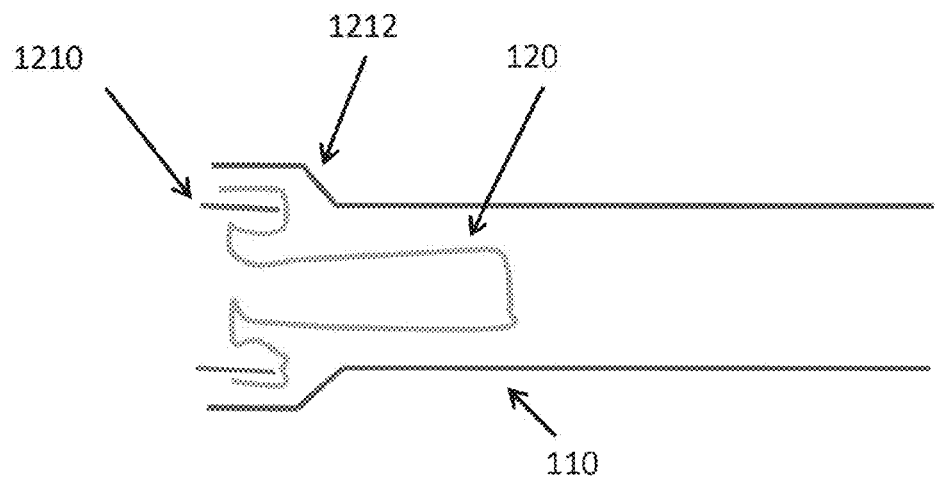

In some embodiments, as shown in FIGS. 12c-12d, the balloon inversion subassembly 1200 may facilitate inversion of balloon 120 out of sleeve 100. For example, balloon 120 may be partially inverted into bushing 1210 prior to insertion of balloon inversion subassembly 1200 into sleeve 110. In some embodiments, the closed end of balloon 120 may be inserted into a tubular mandrel 1216, which can then be advanced into bushing 1210 to at least partially invert balloon 120, as shown in FIG. 12c. The balloon inversion subassembly 1200 may be inserted into sleeve 110 before or after inversion of balloon 120. At least partially inverting balloon 120 may decrease eversion pressure required to deploy balloon 120 out of sleeve 110 during procedure.

Figure 13A:
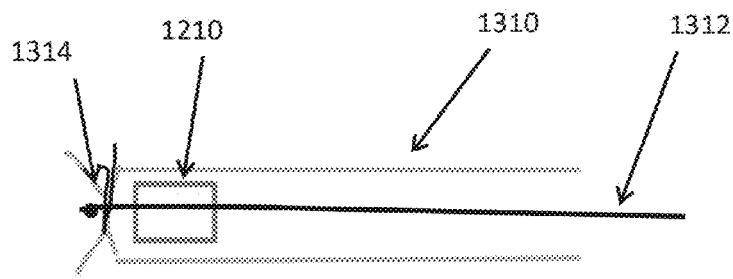
FIGS. 13a-13d illustrate an embodiment method for assembling a system for providing access across an area of obstruction in accordance with an embodiment of the present invention.
Figure 13B:
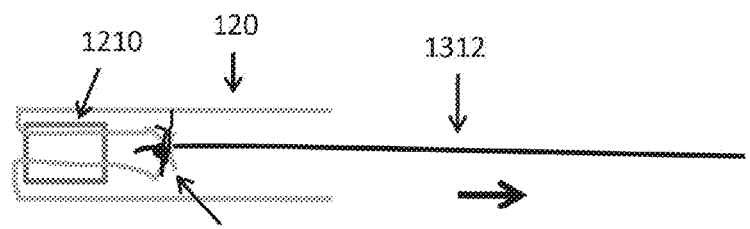
Figure 13C:
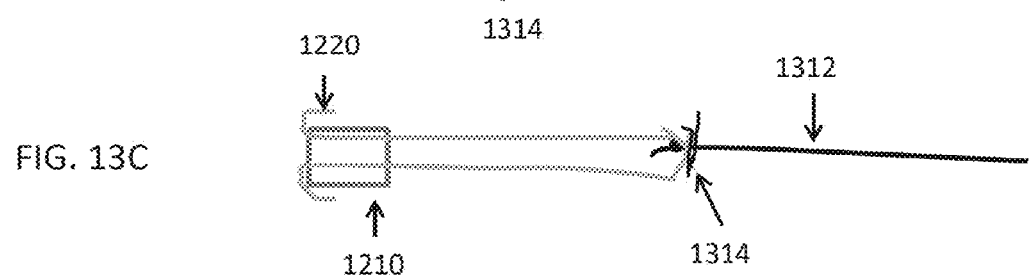
Figure 13D:
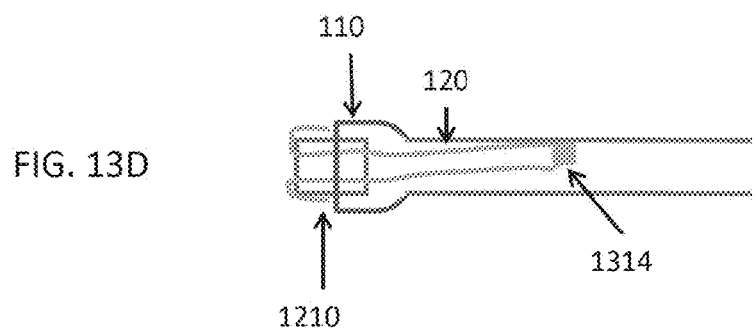

FIGS. 13a-13d illustrate an embodiment of a method of forming balloon insertion subassembly 1200. First, bushing 1210 can be placed inside an open-ended balloon material 1310. A suture 1312 can be passed through the balloon material 1310 and bushing 1210 and can be used to tie a knot at one end 1314 of balloon material 1310 to form balloon 120. By pulling on suture 1312, the tied end 1314 of balloon 120 can be pulled through bushing 1210 until a sufficient length of material is left for anchoring sections 1220, which can be bonded to bushing 1210. In some embodiments, the tied end of balloon 120 can be sealed as shown in FIG. 13d.

Figure 14:
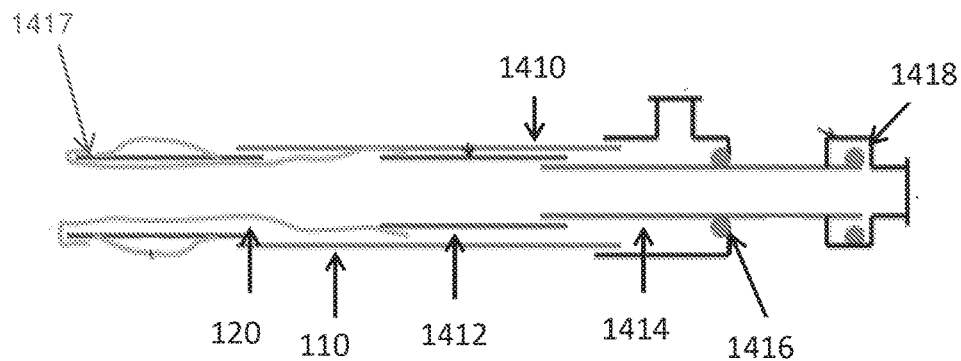
FIG. 14 illustrates a system for providing access across an area of obstruction in accordance with an embodiment of the present invention.

In reference to FIG. 14, in some embodiments, balloon 120 may be deployed manually instead of by eversion pressure to allow the user to exercise more precise control over deployment of balloon 120. In some embodiments, the proximal end of balloon 120 may be connected to a push assembly 1410 slidable within sleeve 110 to allow user to manually advance or retract balloon 120.

In some embodiments, push assembly 1410 may include an inner sleeve member 1412 and a push tube 1414 having a distal end connected to a proximal end of catheter member. In some embodiments, the proximal end of balloon 120 may be connected to the distal end of inner sleeve member 1412. In some embodiments, inner sleeve member 1412 may form a slip fit with the inner lumen of sleeve 110 to permit movement of the inner sleeve member 1412 in longitudinal direction within sleeve 110. In some embodiments, the inner sleeve member 1412 may be equal in length to balloon 120. The proximal end of inner sleeve member 1412 may be connected, in some embodiments, to a push tube 1414 that protrudes proximally out of sleeve 110. In some embodiments, push tube 1414 may be rigid to enable longitudinal displacement of inner sleeve member 1412 as the user pushes on push tube 1414. In some embodiments, a sliding O-ring seal 1416 (also known as a Tuohy-Borst seal) may be provided on the fitting at the proximal end of sleeve 110 to form a seal between push tube 1414 and inner walls of sleeve 110. Such fitting may be a Y-connector having an inflation port and the Tuohy-Borst seal. Push tube 1414 may be constructed of metal such as stainless steel, or a reinforced plastic catheter section that does not collapse within the sliding O-ring seal. In some embodiments, push tube 1414 may be slightly longer than the length of balloon 120, and its proximal end may be connected to a second Tuohy-Borst seal to enable instruments to be passed through push tube 1414. In some embodiments, a Tuohy-Borst seal 1418 on the proximal end of push tube 1414 may be provided to enable passage of guidewire through sleeve 110 during procedure while maintaining hemostasis.

In some embodiments, push assembly 1410 may be configured to limit the extent of balloon eversion and balloon re-inversion. By way of a non-limiting example, in connection with the embodiment of push assembly 1410 described above, balloon eversion may be limited such that only balloon 120 everts through the lesion, and not inner sleeve member 1412 connected to the proximal end of balloon 120. To that end, a bushing 1417 may be used to couple balloon 120 to sleeve 110. As balloon 120 fully everts, the distal end of inner sleeve member 1412 can travel in distal direction until it reaches bushing 1417, which will act as an eversion stop to prevent inner sleeve member 1412 from exiting sleeve 110. Pulling back on push tube 1414 with a partially pressurized catheter may cause balloon 120 to re-invert. In some embodiments, balloon re-eversion may be limited to prevent tear or detachment of balloon 120 from sleeve 110 due to undue traction exerted on balloon 120. In some embodiments, the O-ring seal in the proximal end of sleeve 110 may act to stop limiting re-eversion of balloon 120. As push tube 1414 is retracted through the Tuohy-Borst seal, the proximal end of inner sleeve member 1412 will contact the O-ring seal at full re-eversion of balloon 120, thus limiting unwanted forces on balloon 120. It should of course be noted that other methods may be used to limit the extent of balloon eversion and balloon re-inversion.

Figure 15A:
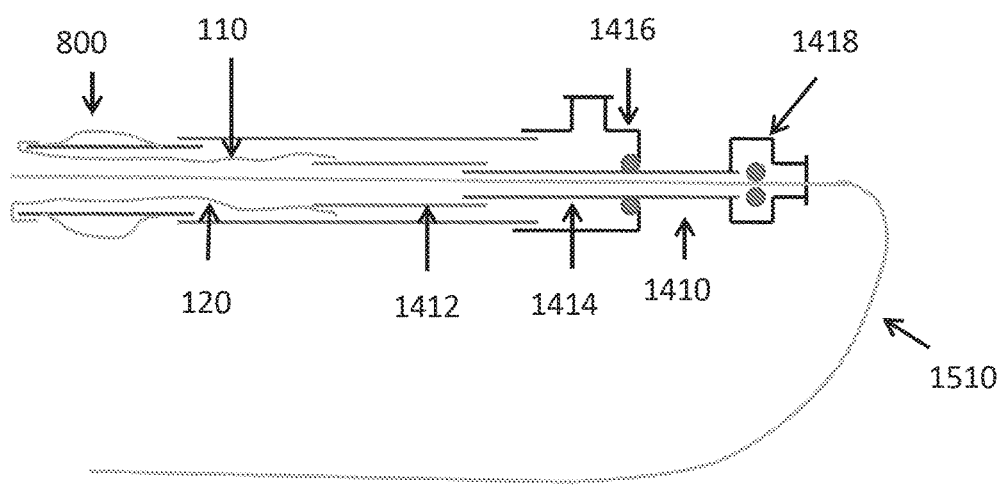
FIGS. 15a-15c illustrate an embodiment method for using a system for providing access across an area of obstruction in accordance with an embodiment of the present invention.
Figure 15B:
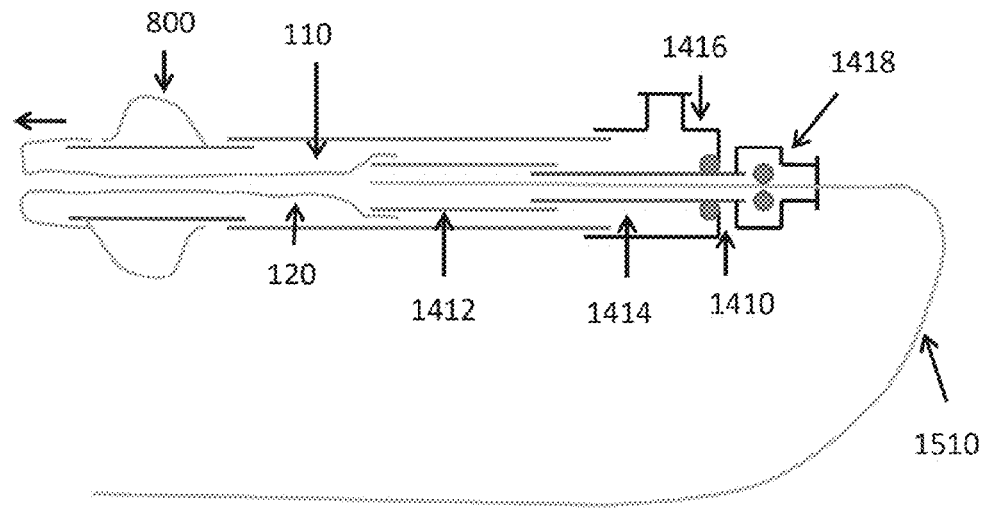
Figure 15C:
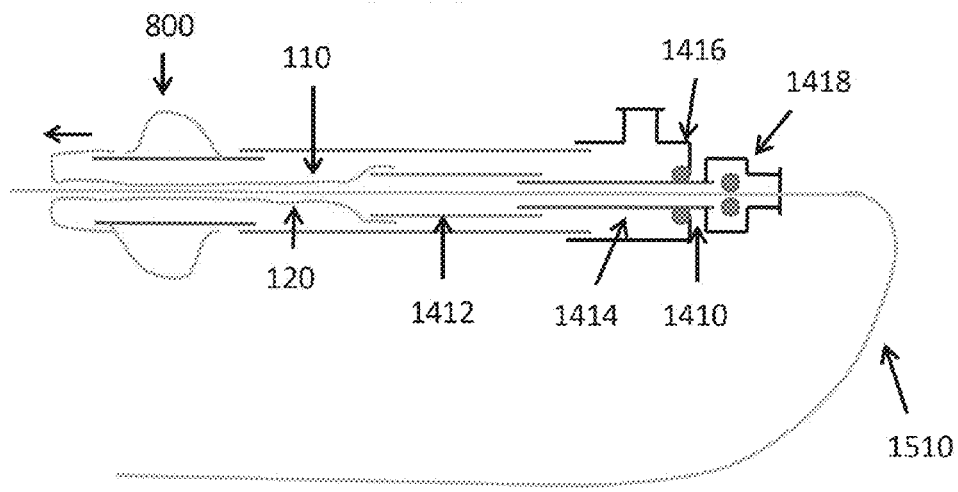

In reference to FIGS. 15A-15C, the systems and devices of the present disclosure may, in some embodiments, be used to open occluded hardened arteries with no residual lumen. The proximal face of such occluded lesions are commonly described as containing a "hard cap", that are typically difficult to penetrate with guidewire. The devices of the present disclosure may be used to assist penetrating such occlusions. In general, a guidewire may be advanced toward distal end of sleeve 110. Sleeve 110 may be pressurized causing balloon 120 to collapse onto the guidewire to securely grip the guidewire. Next, balloon may be repeatedly everted and reinverted to cyclically drive the guidewire tip into the lesion for recanalization. Once a channel is initiated in the hard cap with the guidewire tip, the guidewire may be removed and balloon 120 may be everted into the channel created in the occlusion. If necessary, guidewire of sequentially increasing size may be used to enlarge the channel before balloon 120 may be everted through the channel.

As shown in FIG. 15A, a guidewire 1510 may be loaded into the central lumen of the push assembly 1410 and balloon 120. Upon inflation of sleeve 110, anchoring cuff 800 inflates, and the entire length of balloon 120 may collapse onto guidewire 1510 inside its central lumen to securely grip the guidewire. The O-ring seal of the Tuohy-Borst connector on the proximal end of push assembly 1410 may also be closed onto guidewire 1510. When push assembly 1410 is advanced forward to manually evert balloon 120, balloon 120 may advance guidewire 1510 into the hard cap, while providing a supporting force to enable guidewire to pierce the cap. In some embodiments, balloon 120 may push guidewire 1510 forward a distance equal to the distance of push tube advancement. It should be noted that, in some embodiments, since balloon 120 advances in a toroidal, double walled configuration, balloon 120 advances a distance that is one-half the distance of push tube advancement. In this manner, guidewire 1510 may advance ahead of the leading front of balloon 120 to penetrate the occlusion. In some embodiments, balloon 120 may be everted and inverted sequentially to cyclically pulse guidewire 1510 into the hard cap to create an opening into previously inpenetrable occlusive lesions.

In operation, as noted above, guidewire 1510 may be centered inside sleeve 110 and may be centered within the artery by the inflated anchoring cuff. Moreover, balloon 120 may stabilize guidewire 1510 in such centered position when balloon 120 is pressurized as shown in FIG. 15B. Advancement of push tube 1410 may drive distal tip of guidewire 1510 into the center of the hard cap, to reopen the total occlusion. Once guidewire 1510 has entered a short distance into the occlusion, the push tube may be advanced further to continue the recanalization process.

In some embodiments, push tube 1410 may be cyclically advanced and retracted a short distance; e.g. 5-10 mm at a time, to serially drive a guidewire with higher rigidity into the occlusion. In some embodiments, sleeve 110 may be depressurized and guidewire 1510 pulled back, so upon re-pressurization of sleeve 110, only balloon 120, without guidewire 1510, is advanced through the occlusion. Balloon-only advancement may be performed in situations in which advancement of the guidewire tip preceding the balloon may be dangerous; for example, if vessel curvature or the presence of a bifurcation or branch increases the potential for guidewire perforation.

A system for providing access across a site of obstruction is provided. The system may include a sleeve, having a distal portion that can move from an inverted position to an everted position. A balloon situated within the sleeve can be extended so as to evert sleeve. A pathway can extend across a juncture between the distal portion and the remaining portion of the sleeve so as to provide access across the site of obstruction.

A method for providing access across a site of obstruction is also provided. The method includes positioning an inverted, distal portion of a sleeve adjacent to a site of obstruction. The distal portion may be moved from an inverted position to an everted position so that the distal portion extends across the site of obstruction thereafter. A pathway, extending across a juncture between the distal portion and the remainder of the sleeve, is provided to allow access across the site of obstruction.

In some embodiments, a system for providing access across a site of obstruction is provided. The system may include a sleeve having an inflation lumen. They system may also include an anchoring member coupled to the sleeve, the anchoring member being in fluid communication with the inflation lumen and being expandable from a deflated position to an inflated position to anchor the sleeve near a site of obstruction when the inflation lumen is pressurized to an anchoring pressure sufficient to anchor the sleeve in proximity to a site of obstruction. In some embodiments, the system also includes an everting member movable from an inverted position inside the sleeve to an everted position outside the sleeve due to a pressure increase in the inflation lumen greater than the anchoring pressure.

In some embodiments, a system for providing access across a site of obstruction may include a sleeve having an inflation lumen. The system may further include an anchoring cuff disposed about the sleeve, the anchoring cuff being in fluid communication with the inflation lumen for inflating the anchoring cuff to anchor the sleeve near a site of obstruction, and a balloon in fluid communication with the inflation lumen, the balloon having an everting section movable from an inverted position inside the sleeve to an everted position outside the sleeve when the inflation lumen is pressurized to an eversion pressure.

In some embodiments, in the system of the present disclosure, the sleeve may include a distal portion configured to be moved by the everting member from an inverted position inside the sleeve to an everted position outside the sleeve. In some embodiments, when the distal portion is in the everted position, a pathway is formed extending across a juncture between the distal portion and a remaining portion of the sleeve to provide access across a site of obstruction.

In some embodiments, the system of the present disclosure may further include a puncture wire for opening a distal end of the everting section.

In some embodiments, the everting member may be connected to a distal end of the anchoring member. In other embodiments, the anchoring member may be independent from the everting section.

In some embodiments, the everting member has an outer diameter smaller than an outer diameter of the anchoring member.

In some embodiments, the system of the present disclosure may further include a guidewire sheath positioned about the sleeve and having a lumen through which a guidewire can be advanced between.

In some embodiments, a method of providing access across a site of obstruction is provided. The method may include a step of positioning a sleeve having an inflation lumen adjacent to a site of obstruction. The inflation lumen may pressurized to a first pressure to inflate an anchoring member to anchor the sleeve near the site of obstruction. The inflation lumen may also be pressurized to a second pressure higher than the first pressure to evert an everting section from inside the sleeve through the site of obstruction.

In some embodiments, a distal end of the everting section to provide access across the site of obstruction may be punctured. In some embodiments, a distal portion of the sleeve may be everted with the everting member from an inverted position inside the sleeve to an everted position outside the sleeve and through the site of obstruction to provide access across the site of obstruction.

Although described as proving access across a site of obstruction within a vessel within a body, the invention can provide access across other sites of obstruction as well. For example, the invention can be used to provide access across an obstruction in a cavity or other type of opening. Furthermore, the invention is not limited to use within the medical field. The sleeve can, for instance, be delivered across an obstruction in a cave or other type of passage. Additionally, since the balloon may be designed to seek the path of least resistance, as described above, the invention may be used to seek out hidden or unknown pathways through various sites of obstruction. In other embodiments, the invention may be equipped with an object or device to be delivered across a site of obstruction. In such an embodiment, the device may be situated on the distal portion 114 of sleeve 110, or on a distal end of balloon 120, so that as sleeve 110 everts across and balloon 120 extends through the site of obstruction, the object is delivered to an area distal to the site of obstruction.

While the invention has been described in connection with specific embodiments, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A system for providing access across a site of obstruction comprising:
   a sleeve having a lumen;
   an inner sleeve member slidably disposed within the lumen of the sleeve and limited from exiting a distal end of the sleeve, and having an inner lumen through which a guide wire can be directed;
   an everting member having a distal end coupled to the distal end of the sleeve and a proximal end coupled to the inner sleeve member, the everting member being configured to collapse and securely grip the guide wire when the lumen is pressurized such that advancement of the inner sleeve member pushes the guide wire into the site of obstruction: and
   a bushing disposed in a distal section of the sleeve to couple the everting member to the distal end of the sleeve, wherein the bushing acts as a stop to prevent the inner sleeve member from exiting the distal end of the sleeve.

2. The system of claim 1 further comprising an anchoring member coupled to the sleeve, the anchoring member being in fluid communication with the lumen and being expandable from a deflated position to an inflated position to anchor the sleeve near a site of obstruction when the lumen is pressurized to an anchoring pressure sufficient to anchor the sleeve in proximity to a site of obstruction.

3. The system of claim 1, further comprising a rigid push tube extending proximally from the inner sleeve member.

4. The system of claim 1 further comprising a sealing member disposed between walls of the lumen and the inner sleeve member to seal the lumen.

* * * * *